United States Patent [19]

Foster

[11] Patent Number: 5,897,565
[45] Date of Patent: Apr. 27, 1999

[54] RELEASABLE, SURGICAL CLAMP

[75] Inventor: Thomas L. Foster, Poland, Ind.

[73] Assignee: Vance Products Incorporated, Spencer, Ind.

[21] Appl. No.: 08/399,946

[22] Filed: Mar. 6, 1995

[51] Int. Cl.⁶ .................................................. A61B 17/12
[52] U.S. Cl. ............................................ 606/158; 24/546
[58] Field of Search .................................. 606/151, 157, 606/158, 142, 143; 227/901, 902; 24/530, 532, 533, 545, 546, 547, 549, 555, 551–553, 556, 563, 570, 571

[56] References Cited

U.S. PATENT DOCUMENTS

| | | | |
|---|---|---|---|
| 469,191 | 2/1892 | Sooshny | 24/546 |
| 669,863 | 3/1901 | Simmons | 24/555 |
| 3,996,937 | 12/1976 | Williams | 24/546 |
| 4,367,746 | 1/1983 | Derechinsky | 606/158 |
| 4,660,558 | 4/1987 | Kees, Jr. | 24/546 |
| 5,282,812 | 2/1994 | Suarez, Jr. | 606/158 |

FOREIGN PATENT DOCUMENTS

| | | | |
|---|---|---|---|
| 37 22 311 | 1/1989 | Germany | 606/158 |
| 1192794 | 11/1985 | U.S.S.R. | 606/158 |

OTHER PUBLICATIONS

Copy of Edslab® Parallel Jaw Spring Clip (Model CV5100) with package labeling, manufactured by Baxter Healthcare Corporation, Edwards LIS Division, Irvine, CA 92714–5686.

Bulldog Clamps, AESCULAP® General Catalogue, Tuttlingen, Germany, 1992, pp. 209–211.

Primary Examiner—Michael Powell Buiz
Assistant Examiner—Vikki Trinh
Attorney, Agent, or Firm—Richard J. Godlewski

[57] ABSTRACT

A releasable, surgical clamp (10) for insertion through a surgical introducer sheath (11) and into a cavity (12) of a patient (13) during a minimally invasive surgical procedure. The releasable clamp comprises a continuous wire (39) that is shaped for insertion through the surgical sheath and into opposing jaws (14, 15). The jaws have a plurality of open and closed positions. One of the jaws has a retainer (16) that maintains the lateral displacement (17) between the opposing jaws and prevents the clamp from twisting off a vessel. A resilient assembly (18) including a torsion spring (19) and first and second resilient arms (20, 21) extending to the opposing jaws urges the jaws to a closed position. Each of the resilient arms includes a distal portion which cross each other urging the opposing jaws to a closed position. The clamp further includes a tubular, elongated containment member having a hollow passage (26) that extends therein for receiving the clamp and operating it between its open and closed positions.

22 Claims, 5 Drawing Sheets

RELEASABLE, SURGICAL CLAMP

TECHNICAL FIELD

This invention relates generally to medical devices and, in particular, to a releasable, surgical clamp that is insertable through a surgical introducer sheath and into the cavity of a patient.

BACKGROUND OF THE INVENTION

Temporary ligation of a tubular vessel such as a blood vessel is often required during a surgical procedure. This temporary ligation of a blood vessel is commonly performed using commercially available "bulldog" clamps and forceps. A bulldog clamp typically includes a pair of clamping jaws with a spring positioned between the proximal ends thereof. In use, the spring is compressed using forceps so that the distal ends of the clamping jaws are moved apart. Then the open jaws of the clamp are positioned over the vessel to be ligated. When the clamp is released from the forceps, the spring expands against the proximal ends of the clamping jaws for forcing the jaws together and gripping the vessel positioned therebetween.

A problem with these commercially available clamps is that they are impractical for use in minimally invasive surgical procedures such as laparoscopy, endoscopy, pelviscopy, and hysteroscopy, which utilize an access port with an inside diameter in the range of 5 to 10 mm. The bulldog clamps and forceps are simply too wide to fit through the port. As a result, the clamps cannot be introduced into a body cavity of a patient during a minimally invasive surgical procedure.

Another device for performing temporary ligation of a blood vessel is a V-shaped surgical clamp. The V-shaped clamp is positioned and compressed over a blood vessel using inserter forceps and removed therefrom using separate, remover forceps. A 0.5" (12.7 mm) long V-shaped clamp is recommended for use when temporarily ligating a femoral artery through a 4" (10.16 mm) long incision in the groin of a patient.

Again, a problem with the V-shaped clamp is that it is impractical for introduction with forceps through a minimally invasive access port. The clamp and inserter forceps together are simply too wide to fit through the access port. Another inconvenience of using the V-shaped surgical clamp is that the clamp requires separate forceps for the insertion and removal thereof.

SUMMARY OF THE INVENTION

The foregoing problems are solved and a technical advance is achieved in an illustrative releasable, surgical clamp that is insertable through a minimally invasive surgical introducer sheath and into the cavity of a patient. The surgical clamp comprises a continuous wire that is shaped for insertion through the surgical introducer sheath. The clamp includes opposing jaws having an open and a closed position. One of the jaws has a retainer that advantageously maintains the lateral displacement between the opposing jaws. Furthermore, the retainer minimizes, if not eliminates, the tendency for the surgical clamp to twist off a vessel due to a rotational torque that is created by the laterally displaced jaws. The longitudinally positioned retainer in the preferred embodiment creates a counterbalancing torque with the opposing jaw and stabilizes the clamp on the vessel. The surgical clamp also includes a resilient assembly that is also configured for insertion through the introducer sheath and extends to the opposing jaws and urges them to the closed position in the preferred embodiment.

The resilient assembly includes a torsion spring that urges the opposing jaws to an open or a closed position. The spring includes resilient arms that extend to the opposing jaws. In the preferred embodiment, the spring applies a load to the resilient arms to urge them apart. To translate this separating load, each of the resilient arms advantageously includes an angled distal portion that cross each other and urge the opposing jaws together to the closed position.

The opposing jaws advantageously include an atraumatic distal end to minimize, if not eliminate, trauma to tissue coming in contact therewith. Jaw extensions are attached to the opposing jaws to provide various contact and gripping configurations.

The releasable, surgical clamp of the present invention further includes a tubular, elongated containment member that is configured for insertion through the surgical introducer sheath. The tubular containment member has a hollow passage extending therein that is configured to receive the resilient assembly of the clamp. The elongated containment member also includes an engagement member that is positioned in the hollow passage and is extendable from the containment member to engage and urge the resilient assembly into the hollow passage.

The tubular containment member also includes a deflector positioned in the hollow passage and configured to engage the resilient member and to transition the opposing jaws between the open and closed positions. In the preferred embodiment, the deflector includes an annular recess in the tubular containment member and extends a projection or camming surface into the hollow passage of the containment member. In another aspect of the invention, the deflector includes a slotted sleeve positioned in the hollow passage through which the engagement member passes. To orient the releasable clamp with respect to the engagement member, opposing longitudinal recesses are positioned at the distal end of the containment member substantially perpendicular to the engagement member to receive and position the resilient arms of the clamp therein.

DETAILED DESCRIPTION

Figure 1:
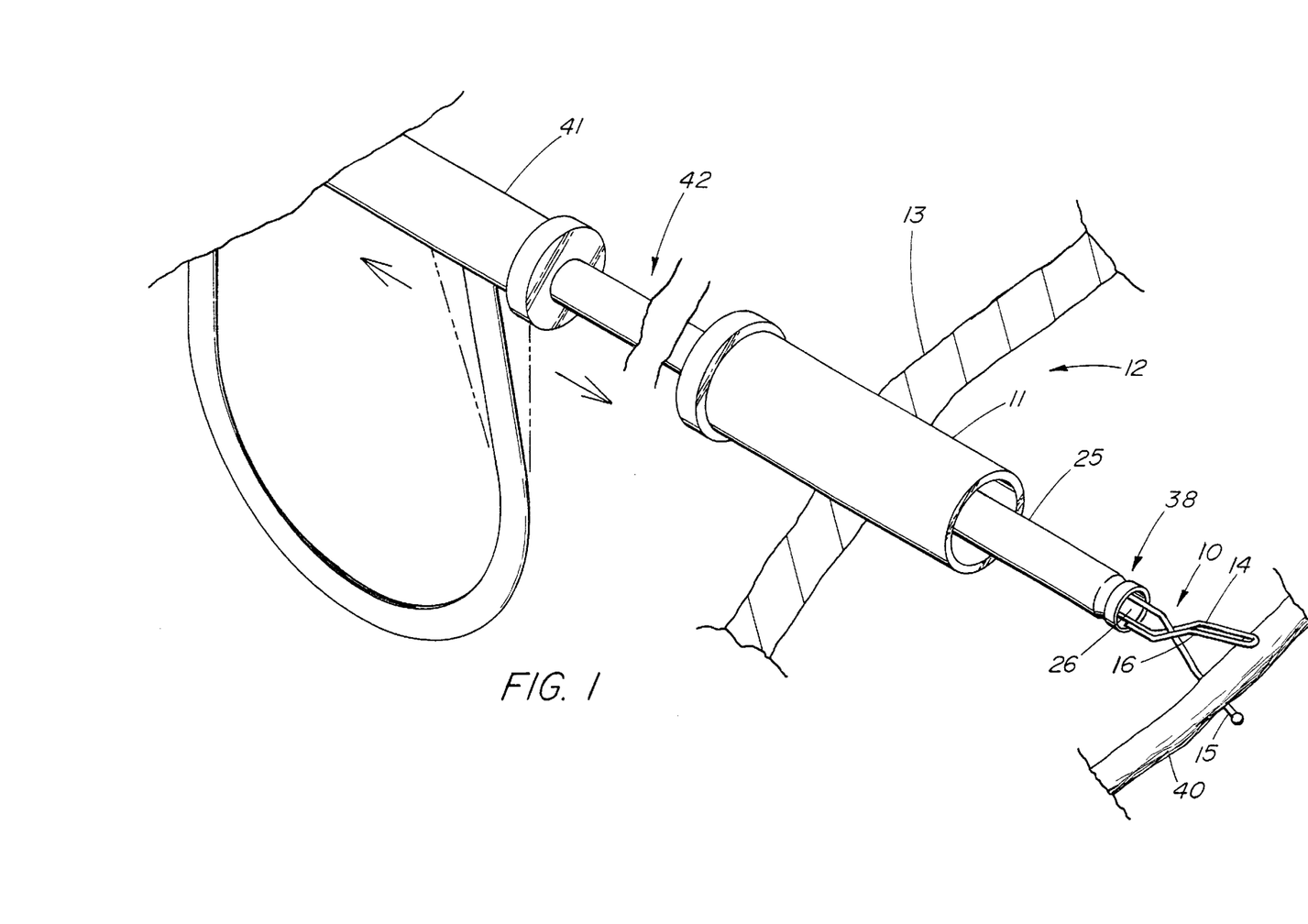
FIG. 1 is a preferred embodiment of a releasable, surgical clamp of the present invention that is inserted through a surgical introducer sheath and into the cavity of a patient.
Figures 2, 3, 4:
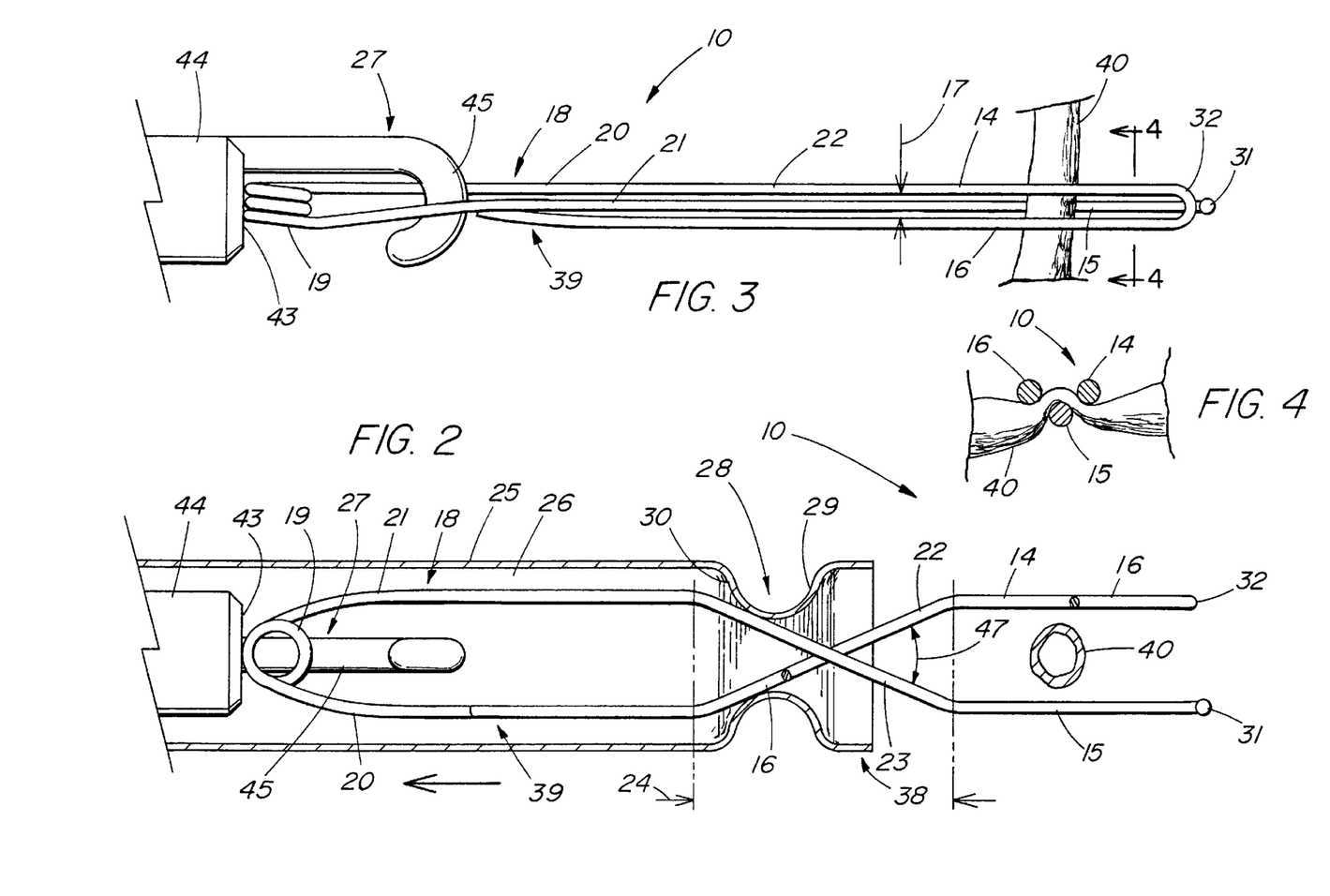
FIG. 2 depicts an enlarged, side view of the releasable clamp of FIG. 1.
FIG. 3 depicts a top view of the releasable clamp of FIG. 2 in a closed position clamping a vessel.
FIG. 4 depicts a cross-sectioned view of the releasable clamp of FIG. 3 along the line 4—4.

Depicted in FIG. 1 is a preferred embodiment of releasable, surgical clamp 10 that is inserted through minimally invasive surgical introducer sheath 11 and into cavity 12 of patient 13. Opposing jaws 14 and 15 of the clamp are in an open position and are positioned about vessel 40 in anticipation of clamping the vessel. The releasable clamp is positioned in hollow passage 26 of minimally invasive applicator 42 about distal end 38 thereof. The applicator includes tubular, elongated containment member 25 that contains the releasable clamp and is configured for the passage of the tubular member and the releasable clamp through the introducer sheath. The applicator also includes a handle 41 that is positioned at the proximal end of the tubular containment member for drawing tubular containment member 25 rearward and releasing clamp from hollow passage 26. The handle is more fully described in U.S. Pat. No. 5,376,096 of the present inventor, the description therein being incorporated by reference herein. When released from the tubular containment member, the opposing jaws of the releasable clamp assume a closed position and clamp vessel 40 as depicted in FIGS. 3 and 4. To minimize, if not eliminate, twisting the clamp off of vessel 40 due to rotational torque caused by the laterally displaced jaws, the releasable clamp includes retainer member 16 that is positioned longitudinally alongside jaw 14. In addition, the retainer member also maintains the lateral displacement between opposing jaws 14 and 15 when in the open and closed positions and when transitioning therebetween.

FIG. 2 depicts an enlarged, side view of clamp 10 of FIG. 1. The clamp is positioned in hollow passage 26 about partially sectioned distal end 38 of tubular, elongated containment member 25. Releasable clamp 10 is in a partially opened position with angled distal portions 22 and 23 of respective resilient arms 20 and 21 engaging annular projection surface 30 of the containment member. Annular projection surface 30 can also be described as a camming surface. Engagement of distal portions 22 and 23 of resilient arms 20 and 21 with annular projection surface 30 operates opposing jaws 14 and 15 between fully opened and closed positions as the position of the annular projection surface is longitudinally changed with respect to the clamp. This is accomplished by the physician pulling on the applicator handle and drawing the containment member proximally with respect to the clamp. To maintain the clamp in a fixed relative longitudinal position, the proximal end of the clamp engages flat end surface 43 of push rod 44. Flat end surface 43 is positioned transversely to the longitudinal axis of tubular containment member 25. In addition to push rod 44, engagement member 27 includes an engagement finger 45. The finger is hook-shaped about its distal end and extends distally from push rod 44. The proximal end of the finger is attached in a well-known, parallel manner to the push rod. The engagement finger is extendable distally from the distal end of the tubular containment member and, when so extended, is used to engage and open releasable clamp 10.

Elongated tubular member also includes a deflector 28 to engage the releasable clamp and operate it between its open and closed positions. In this preferred embodiment, the deflector includes an annular recess 29 that is swaged or crimped into the tubular containment member near distal end 38 thereof. As a result, annular projection surface 30 is formed in hollow passage 26 of the tubular containment member for engaging distal portions 22 and 23 of resilient arms 20 and 21, respectively. By way of example, tubular, elongated containment member 25 is a 6.5 gauge thin-wall stainless steel tube with an outside diameter of approximately 0.187" and an inside diameter of approximately 0.165". Deflector 28 comprises an annular recess 29 having a radius of approximately 1/32" swaged or crimped into the stainless steel tube with the center of the radius approximately 0.100" from distal end 38 of the tube. Hollow passage 26 has a minimum diameter of approximately 0.125" at camming or projection surface 30. Stainless steel push rod has a 0.156" diameter longitudinally recessed about its distal end to accept the proximal end of stainless steel engagement finger 45 that has an approximately 0.048" diameter. For ease of capturing the closed clamp, the end of the finger is approximately 0.225" from flat end surface 43 of the push rod.

Releasable clamp 10 is formed from a continuous piece of approximately 0.025" diameter, series 300 stainless steel cylindrical wire 39 having an overall length of approximately 3.1" before bending. The clamp as depicted has a preferred overall length of approximately 1.0" with a range of 0.800 to 1.050". The outside width of the clamp with opposing jaws 14 and 15 in a parallel configuration is approximately 0.135".

Releasable clamp 10 also includes a resilient assembly 18 that extends to and urges opposing jaws 14 and 15 to an open or a closed position and, in particular, to a preferred closed position. The resilient assembly includes torsion spring 19 having resilient arms 20 and 21 extending therefrom and urging opposing jaws 14 and 15 to a closed position, respectively.

Figure 5:
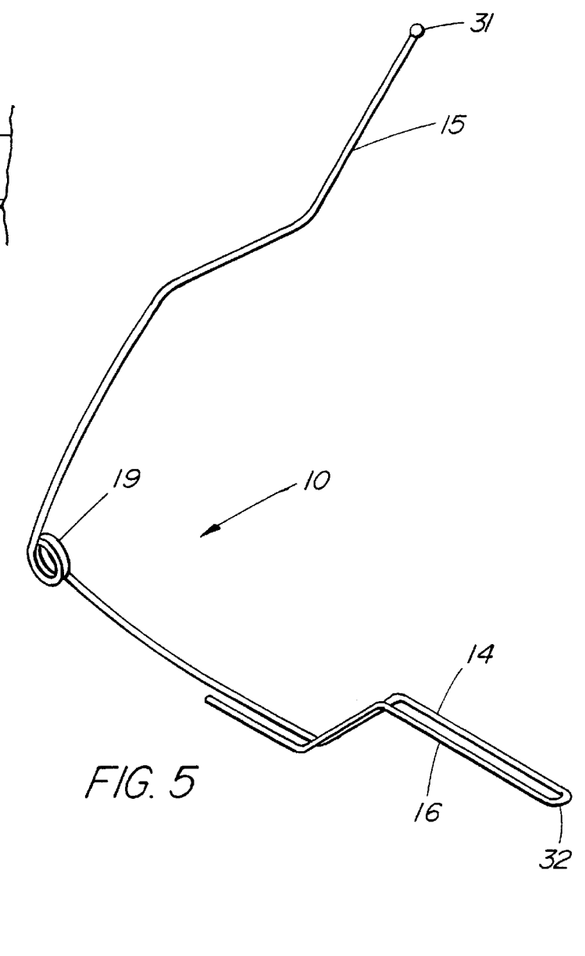
FIG. 5 depicts the releasable clamp of FIG. 2 with the torsion spring thereof in a relaxed condition.

FIG. 5 depicts releasable clamp 10 of FIG. 2 with torsion spring 19 in a relaxed condition. In this relaxed condition, torsion spring 19 comprises two and one-quarter turns of the continuous wire with an inside diameter of approximately 0.050" and an overall length of approximately 0.075". Additional or less turns can be utilized depending on the desired clamping force; however, the length of the coil cannot exceed 0.125" so as to pass through hollow passage 26 at projection surface 30. Opposing jaws 14 and 15 of the clamp in the relaxed condition are brought together and overlapped, thereby loading torsion coil 19. The distal ends of the opposing jaws are overlapped to maintain the jaws in a closed position. Retainer member is formed from the continuous wire and is longitudinally positioned along one side of jaw 16. The bend between jaw 14 and retainer member 16 presents an atraumatic distal end 32 to prevent or to minimize trauma to tissue coming in contact with the clamp. Similarly, an approximately 0.0401" ball of material is applied in a well-known manner to the distal end of jaw 15 to form atraumatic tip 31. Retainer member maintains the lateral displacement between opposing jaws 14 and 15 when in and transitioning between open and closed positions. Opposing jaws 14 and 15 extend longitudinally for approximately 0.250". Resilient arms 20 and 21 longitudinally extend for the remainder of the length of the clamp. Angled portions 22 and 23 of respective resilient arms 20 and 21 extend longitudinally for a distance 24 of approximately 0.250" and cross each other to translate the spreading force or load being exerted by torsion coil spring 19 on resilient arms 20 and 21 to a closing force or load on opposing jaws 14 and 15. As also depicted, distal portions 22 and 23 are inclined with respect to each other and form a reference angle 47 of approximately 23 degrees therebetween. Retainer member 16 extends longitudinally along jaw 14 and resilient arm 20 approximately 0.750" from atraumatic distal end 32.

FIG. 3 depicts a top view of releasable clamp 10 of FIG. 2 in a closed position clamping vessel 40. Tubular containment member 25 has been withdrawn proximally from engagement member 27, thereby allowing releasable clamp 10 to assume the closed position clamping vessel 40 with opposing jaws 14 and 15. Lateral displacement 17 between jaw 14 and retainer 16 is maintained at a minimum of 0.025"; however, to minimize rotational torque, the lateral displacement should not exceed 0.050". Engagement member 27 including engagement finger 45 is also used to engage and urge the releasable clamp into tubular containment member 25, when the clamp is in a closed position clamping a vessel. Engaging the clamp in this manner opens opposing jaws 14 and 15 when clamped around a vessel.

FIG. 4 depicts a cross-sectioned view of releasable clamp 10 of FIG. 3 along the line 4—4. Vessel 40 is clearly shown as being clamped between opposing jaws 14 and 15. Similarly, vessel 40 is also clamped between jaw 15 and retainer 16. The rotational torque formed between jaw 15 and opposing jaw 14 is counterbalanced with the rotational torque between jaw 15 and opposing retainer 16, thereby maintaining the clamp in a stable position about vessel 40 with little, if any, concern for the releasable clamp twisting off vessel 40.

Figure 6:
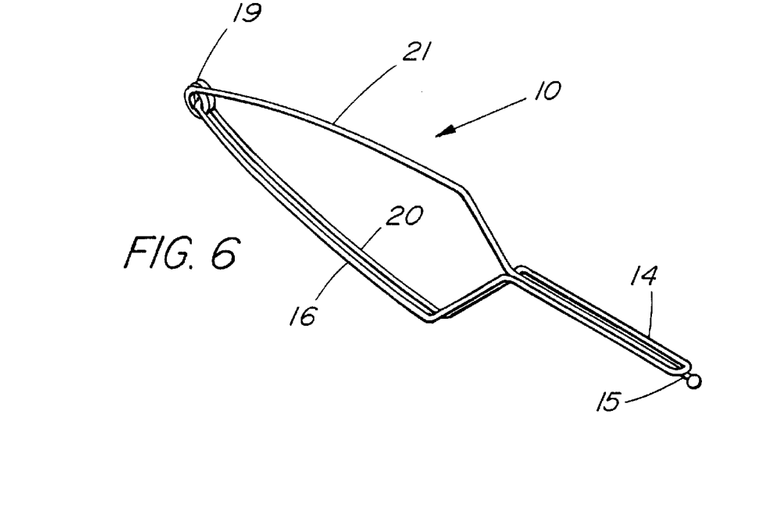
FIG. 6 depicts an alternative embodiment of the releasable clamp of the present invention in which the retainer member has been longitudinally extended to and inserted in the torsion spring of the clamp.

FIG. 6 depicts an alternative embodiment of releasable clamp 10 of the present invention in which retainer member 16 has been longitudinally extended to and the end thereof inserted in torsion coil spring 19. This advantageously allows a greater compression force to be exerted between opposing jaws 14 and 15 as well as retainer 16 extending longitudinally along opposing jaw 14 and resilient arm 20. In this alternative embodiment, the clamp is formed from an approximately 0.025" diameter, series 304 stainless steel, continuous cylindrical wire approximately 3.1" in length. The clamping force is increased due to the selection of the continuous wire material and permits the shortening of the overall length of the clamp to approximately 0.800". The length of the opposing jaws 14 and 15 remains the same as previously described. A test was conducted to determine the clamping pressure of the releasable clamp when it is open approximately 0.100" at a point midway between opposing jaws 14 and 15. A comparison test was also performed on the Baxter Edslab parallel jaw spring clamp model CV5100. The tests were performed on an Instron 4301 test instrument with a 100 pound load cell. An average spring pressure of 5.417, 5.642, and 6.817 was noted for each of three samples of releasable clamp 10.

Figure 7:
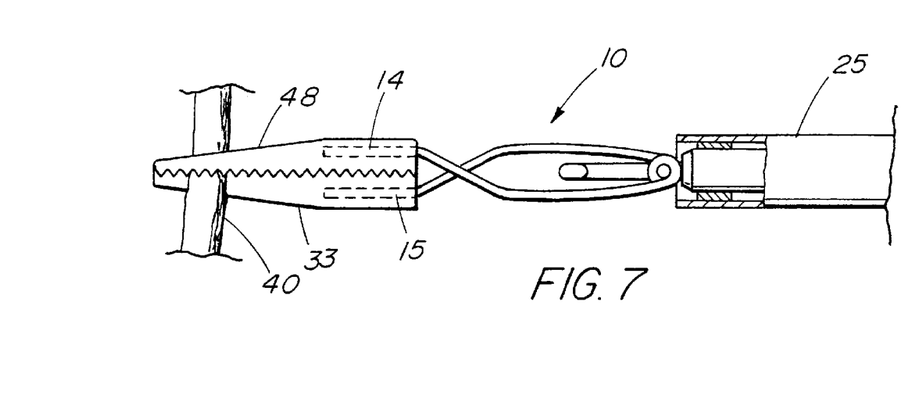
FIG. 7 depicts another alternative embodiment of the releasable clamp of the present invention with jaw extensions.

FIG. 7 depicts another alternative embodiment of releasable clamp 10 of the present invention extended from tubular containment member 25 and clamping vessel 40. Opposing jaws 14 and 15 include jaw extensions 33 and 48, respectively. These jaw extensions similar to alligator clips are attached to opposing jaw 14 and 15. The jaw extensions grasp and clamp vessel 40 as shown.

Figure 8:
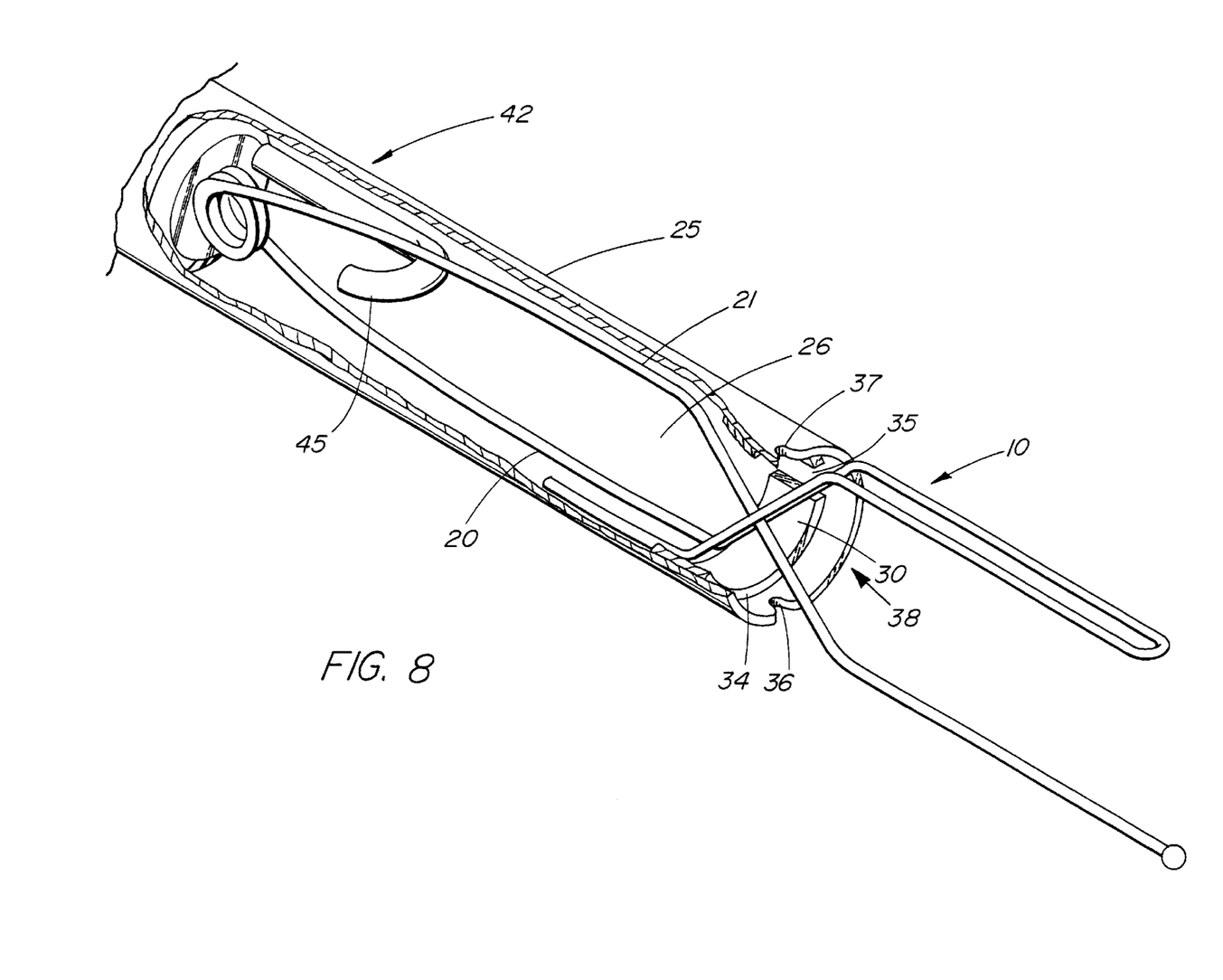
FIG. 8 depicts an alternative embodiment of the applicator of the present invention.

FIG. 8 depicts an alternative embodiment of applicator 42 with releasable clamp 10 positioned in hollow passage 26. Tubular containment member 25 includes projection surface 30 positioned in hollow passageway 26. The projection surface is formed from a tubular sleeve 34 with a longitudinal slot 35 extending longitudinally therein. The longitudinal slot in the sleeve allows engagement finger 45 to pass therethrough without any deflection thereof. The tubular sleeve is positioned in the hollow passage. Since the tubular sleeve can present an abrupt transition to resilient arms 20 and 21, longitudinal recesses 36 and 37 are positioned oppositely at distal end 38 of the containment tube. These longitudinal recesses engage and guide resilient arms 20 and 21 when capturing and withdrawing clamp 10 into hollow passage 26. These recesses are designed to maintain the orientation of the clamp perpendicular to longitudinal slot 35.

Figure 9:
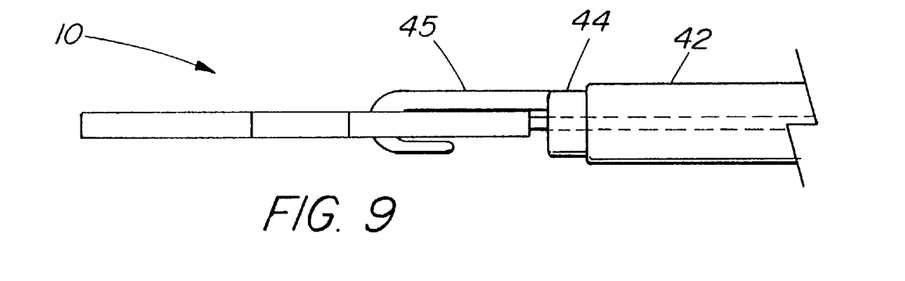
FIGS. 9 through 12 depict still another embodiment of the releasable clamp and applicator of the present invention in various open and closed positions.
Figure 10:
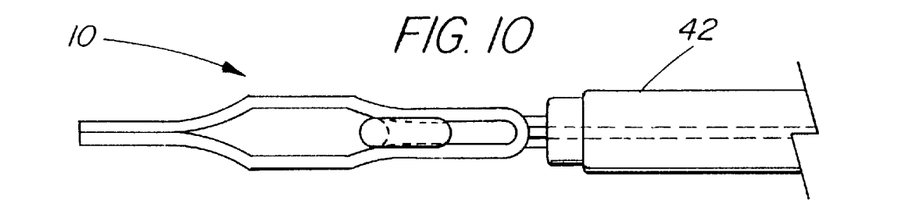
Figure 11:
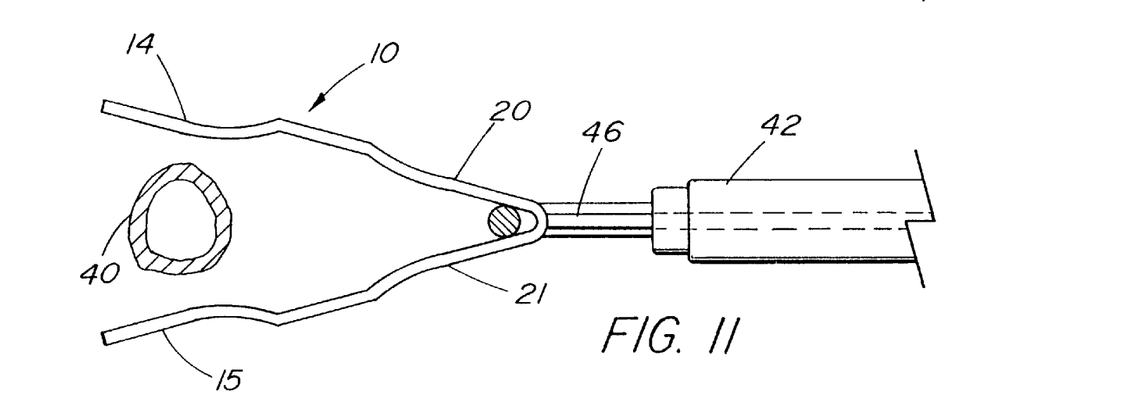
Figure 12:
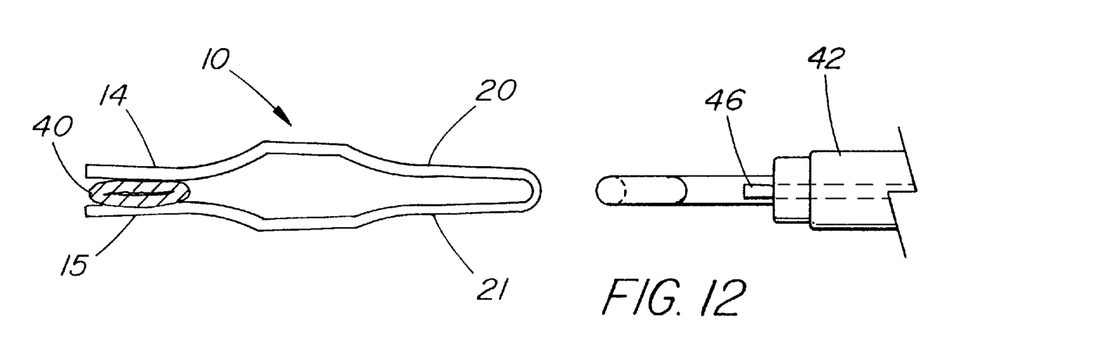

FIGS. 9 through 12 depict still another embodiment of releasable clamp 10 and applicator 42 in various open and closed positions engaging and clamping vessel 40. In this embodiment, releasable clamp 10 is comprised of a continuous U-shaped flat wire. FIGS. 9 and 10 show respective top and side views of the releasable clamp with push rod 44 and engagement finger 45 inserted in the open space of the closed clamp. In FIG. 11, the engagement finger is used to spread resilient arms 20 and 21 apart when slide pin 46 is extended from the push rod. In the open position, opposing jaws 14 and 15 are positioned about vessel 40. FIG. 12 depicts releasable clamp in a closed position with opposing jaws 14 and 15 clamping vessel 40. Slide pin 46 has been withdrawn proximally to permit resilient arms 20 and 21 along with opposing jaws 14 and 15 to collapse on vessel 40.

It is to be understood that the above-described releasable, surgical clamp is merely an illustrative embodiment of the principles of this invention and that other releasable, surgical clamps may be devised by those skilled in the art without departing from the spirit and scope of this invention. It is contemplated that the clamping force can be varied depending on the selection of the continuous wire material and the overall length of the clamp. The length of the opposing jaws and retainer can also be varied in combination with the lengths of the resilient arms. As also depicted, the opposing jaws of the releasable clamp can be biased to either an open or a closed position. This bias or load can be translated by the resilient arms depending on whether the resilient assembly exerts a spreading or contracting load on the resilient arms thereof.

What is claimed is:

1. A surgical device for minimally invasive procedures comprising:
   a surgical introducer sheath (11) for establishing access to a cavity (12) of a patient (13); and
   a releasable, surgical clamp (10) particularly adapted for facile introduction into, complete containment in and facile removal from the body of the patient (13) that is insertable through the surgical introducer sheath (11) and into the cavity (12) of the patient (13);
   wherein the clamp (10) comprises:
      first and second opposing jaws (14, 15) configured for insertion through the surgical introducer sheath (11) and having an open and a closed position, at least one of said opposing jaws (14 or 15) having a retainer (16) that forms an elongated loop having an atraumatic distal end (32) and that maintains a lateral displacement (17) between said opposing jaws (14, 15), said opposing jaws including said retainer engaging a vessel in at least three separated points when the vessel is positioned therein; and
      a resilient assembly (18) configured for insertion through the surgical introducer sheath and engagement therewith, extending to said opposing jaws (14, 15), and urging said opposing jaws (14, 15) to at least one of said open and said closed positions when engaging the surgical introducer sheath;
   whereby the clamp (10) can be contained completely within the cavity (12) of the patient (13) during engagement with the vessel.

2. The device of claim 1 wherein said resilient assembly includes a spring (19) urging said opposing jaws to said at least one of said open and said closed positions.

3. The device of claim 1 wherein said resilient assembly comprises a spring (19) having first and second arms (20,21) extending to said first and second opposing jaws, respectively, and urging said opposing jaws to said at least one of said open and said closed positions.

4. The device of claim 3 wherein said spring urges said first and second arms apart and wherein a distal portion (22) of said first arm and a distal portion (23) of said second arm cross each other urging said opposing jaws to said closed position.

5. The device of claim 1 wherein said resilient assembly includes first and second resilient arms (20,21) extending to said first and second opposing jaws, respectively, and urging said opposing jaws to said at least one of said open and said closed positions.

6. The device of claim 5 wherein said first and second resilient arms are spread apart in response to a load applied thereto and wherein a distal portion (22) of said first resilient arm and a distal portion (23) of said second resilient arm cross each other urging said opposing jaws to said closed position.

7. The device of claim 6 wherein the distal portions of said resilient arms are inclined to each other for a prescribed longitudinal length (24).

8. The device of claim 6 wherein said resilient assembly includes a torsion spring extending to said first and second resilient arms.

9. The device of claim 1 wherein said retainer extends longitudinally along at least one said opposing jaws.

10. The device of claim 1 wherein at least one of said opposing jaws includes an atraumatic distal end (31, 32).

11. The device of claim 1 further comprising an elongated containment member configured for insertion through the surgical introducer sheath, having a hollow passage (26) extending therein that is configured to receive said resilient assembly.

12. The device of claim 11 wherein said elongated containment member includes an engagement member (27) positioned in said hollow passage, extendable from said containment member, and engageable with said resilient assembly to urge said resilient assembly into said hollow passage.

13. The device of claim 12 wherein said containment member also includes a deflector (28) positioned in said hollow passage and configured to engage said resilient member and to transition said opposing jaws between said open and said closed positions.

14. The device of claim 13 wherein said deflector comprises an annular recess (29) in said containment member that extends a projection (30) into said hollow passage of said containment member.

15. The device of claim 1 wherein said opposing jaws and said resilient assembly comprise a continuous wire (39).

16. A surgical device for minimally invasive procedures, comprising:
  a surgical introducer sheath (11) for establishing access to a cavity (12) of a patient (13); and
  a releasable, surgical clamp (10) particularly adapted for facile introduction into, complete containment in and facile removal from the body of the patient (13) that is insertable through the surgical introducer sheath (11) and into the cavity (12) of the patient (13);
  wherein the clamp (10) comprises:
    first and second opposing jaws (14, 15) configured for insertion through the surgical introducer sheath (11) and having an open and a closed position, one of said jaws (14 or 15) having a retainer (16) that forms an elongated loop having an atraumatic distal end (32) and that maintains a lateral displacement (17) between opposing jaws (14 and 15); and
    a torsion spring (19) configured for insertion through the surgical introducer sheath (11) and engagement therewith and having first and second arms (20, 21) extending to said first and second opposing jaws (14, 15), respectively, and urging said first and second opposing jaws (14, 15) to one of said open and said closed positions when said arms engage the surgical introducer sheath;
  whereby the clamp (10) can be contained completely within the cavity (12) of the patient (13) during engagement with the vessel.

17. The device of claim 15 wherein at least one of said opposing jaws includes an atraumatic distal end (31, 32).

18. The device of claim 16 wherein said torsion spring urges said arms apart and wherein a distal portion (22) of said first arm and a distal portion of said second arm cross each other.

19. The device of claim 16 further comprising an elongated tubular containment member (25) having a hollow passage (26) therein configured to receive said torsion spring and an annular recess (29) in said tubular containment member extending a projection (30) into said hollow passage, said projection configured to engage said arms and transition said opposing jaws between said open and said closed positions.

20. The device of claim 16 wherein said opposing jaws and said torsion spring are shaped from a continuous wire (34).

21. A surgical device for minimally invasive procedures comprising:
  (a) a releasable, surgical clamp (10) that is insertable through a surgical introducer sheath (11) and into a cavity (12) of a patient (13), the clamp (10) comprising:
    first and second opposing jaws (14, 15) having an open and a closed position, one of said opposing jaws having an atraumatic distal end (31) and a retainer (16) that maintains a lateral displacement (17) between said opposing jaws when said opposing jaws are in said open and said closed positions, and the other of said opposing jaws having an atraumatic distal end (32); and
    a torsion coil spring (19), first and second arms (20, 21) extending therefrom and to said first and second opposing jaws, respectively, and urging said first and second opposing jaws to said closed position, a distal portion of said first arm and a distal portion of said second arm being inclined to and crossing each other; and
  (b) an elongated tubular containment member (25) configured for insertion through a surgical introducer sheath (11) and having a hollow passage (26) therein to receive said torsion coil spring and also having an annular recess (29) in said tubular containment member extending a projection (30) into said hollow passage, said projection configured to engage said first and second arms and transition said first and second opposing jaws between said open and said closed positions, and an engagement member (27) positioned in said hollow passage of said hollow containment member, extendable from said hollow passage, and engageable with said torsion coil spring to urge said torsion coil spring into said hollow passage;
  whereby the clamp (10) can be contained completely within the cavity (12) of the patient (13) during engagement with the vessel.

22. A surgical device for minimally invasive procedures comprising:

a surgical introducer sheath (11) for establishing access to a cavity (12) of a patient (13); and a releasable, surgical clamp (10) particularly adapted for facile introduction into, complete containment in and facile removal from the body of the patient (13) that is insertable through the surgical introducer sheath (11) and into the cavity (12) of the patient (13);

wherein the clamp (10) comprises:

a continuous wire (39) shaped for insertion through the surgical introducer sheath and engagement therewith and shaped into first and second opposing jaws (14, 15), at least one of said opposing jaws (14 or 15) having a retainer that maintains a lateral displacement (17) between said opposing jaws (14, 15), and a resilient assembly urging said opposing jaws (14, 15) to at least one of an open and a closed position when said resilient assembly engages the surgical introducer sheath;

whereby the clamp (10) can be contained completely within the cavity (12) of the patient (13) during engagement with the vessel.

\* \* \* \* \*